US010478085B2

(12) United States Patent
Nambu et al.

(10) Patent No.: US 10,478,085 B2
(45) Date of Patent: Nov. 19, 2019

(54) APPARATUS FOR ACQUIRING ELECTRIC ACTIVITY IN THE BRAIN AND UTILIZATION OF THE SAME

(71) Applicant: INTER-UNIVERSITY RESEARCH INSTITUTE CORPORATION NATIONAL INSTITUTES OF NATURAL SCIENCES, Mitaka-shi, Tokyo (JP)

(72) Inventors: Atsushi Nambu, Okazaki (JP); Satomi Chiken, Okazaki (JP); Yukio Nishimura, Okazaki (JP); Sayuki Takara, Okazaki (JP)

(73) Assignee: INTER-UNIVERSITY RESEARCH INSTITUTE CORPORATION NATIONAL INSTITUTES OF NATURAL SCIENCES, Tokyo (JP)

( * ) Notice: Subject to any disclaimer, the term of this patent is extended or adjusted under 35 U.S.C. 154(b) by 0 days.

(21) Appl. No.: 16/101,099

(22) Filed: Aug. 10, 2018

(65) Prior Publication Data
US 2019/0038168 A1    Feb. 7, 2019

Related U.S. Application Data

(63) Continuation of application No. 14/433,431, filed as application No. PCT/JP2013/077107 on Oct. 4, 2013, now abandoned.

(30) Foreign Application Priority Data

Oct. 5, 2012 (JP) ................................ 2012-223564

(51) Int. Cl.
*A61N 1/00*    (2006.01)
*A61B 5/0478*    (2006.01)
(Continued)

(52) U.S. Cl.
CPC ........ *A61B 5/0478* (2013.01); *A61B 18/1477* (2013.01); *A61N 1/0529* (2013.01);
(Continued)

(58) Field of Classification Search
CPC ................ A61N 1/0529; A61N 1/0534; A61N 1/36135; A61N 1/36082; A61B 5/0478;
(Continued)

(56) References Cited

U.S. PATENT DOCUMENTS 5,713,922 A    2/1998    King
6,129,685 A *  10/2000   Howard, III ....... A61N 1/36036
                                                    600/373
(Continued)

FOREIGN PATENT DOCUMENTS

JP    2001-510354 A    7/2001
JP    2006-334106 A    12/2006
(Continued)

OTHER PUBLICATIONS

Jan. 7, 2014 International Search Report issued in International Application No. PCT/P2013/077107.
(Continued)

*Primary Examiner* — Mallika D Fairchild
(74) *Attorney, Agent, or Firm* — Oliff PLC

(57) ABSTRACT

The present disclosure provides an apparatus including: one or more needle-like bases enabled to be inserted into the brain; a first electrode having a first impedance and enabling an input of an electric activity of a nucleus with which the first electrode comes into contact; and a second electrode having a second impedance lower than the first impedance and being able to output an electric stimulation to the nucleus, wherein the first electrode is provided at a tip portion of at least one of the bases, and the second electrode is provided on a part of the at least one of the bases at a
(Continued)

position identical to a position of at least one of the first electrode or on a proximal side with respect to the first electrode, in a direction along a long axis of the base on which the first electrode is provided.

12 Claims, 10 Drawing Sheets

(51) Int. Cl.
| | |
|---|---|
| *A61N 1/05* | (2006.01) |
| *A61B 18/14* | (2006.01) |
| *A61N 1/36* | (2006.01) |
| *A61B 5/0484* | (2006.01) |
| *A61B 18/00* | (2006.01) |

(52) U.S. Cl.
CPC ....... *A61N 1/0534* (2013.01); *A61N 1/36135* (2013.01); *A61B 5/0484* (2013.01); *A61B 2018/00446* (2013.01); *A61B 2018/00595* (2013.01); *A61B 2018/00642* (2013.01); *A61B 2018/00839* (2013.01); *A61N 1/36082* (2013.01)

(58) Field of Classification Search
CPC .............. A61B 5/0484; A61B 18/1477; A61B 2018/00642; A61B 2018/00446; A61B 2018/00595; A61B 2018/00839
See application file for complete search history.

(56) References Cited

U.S. PATENT DOCUMENTS

| | | |
|---|---|---|
| 2008/0027504 A1 | 1/2008 | Bedenbaugh |
| 2008/0215125 A1 | 9/2008 | Farah et al. |
| 2010/0274237 A1 | 10/2010 | Yamakawa et al. |
| 2011/0005069 A1 | 1/2011 | Pianca |
| 2011/0160797 A1 | 6/2011 | Makous et al. |
| 2011/0264165 A1 | 10/2011 | Molnar et al. |
| 2011/0270348 A1* | 11/2011 | Goetz ................ A61N 1/00 607/45 |
| 2012/0046715 A1 | 2/2012 | Moffitt et al. |
| 2012/0191157 A1 | 7/2012 | Stypulkowski et al. |

FOREIGN PATENT DOCUMENTS

| | | |
|---|---|---|
| JP | 2007-325652 A | 12/2007 |
| JP | 2009-545402 A | 12/2009 |
| JP | 2010-200875 A | 9/2010 |
| JP | 2011-036360 A | 2/2011 |
| JP | 2012-508635 A | 4/2012 |
| JP | 2012-510877 A | 5/2012 |
| JP | 2012-520159 A | 9/2012 |
| WO | 97/45157 A1 | 12/1997 |
| WO | 2008/016881 A2 | 2/2008 |
| WO | 2009/125535 A1 | 10/2009 |
| WO | 2010/055421 A1 | 5/2010 |
| WO | 2010/065888 A2 | 6/2010 |
| WO | 2010/105261 A2 | 9/2010 |
| WO | 2011/013041 A1 | 2/2011 |
| WO | 2011/136870 A1 | 11/2011 |

OTHER PUBLICATIONS

Jan. 7, 2014 Written Opinion issued in International Application No. PCT/P2013/077107.
Oct. 24, 2014 International Preliminary Report on Patentability issued in International Application No. PCT/P2013/077107.
Jul. 17, 2017 Office Action Issued in U.S. Appl. No. 14/433,431.
Jul. 11, 2017 Office Action issued in Japanese Patent Application No. 2014-539850.
Apr. 10, 2018 Office Action issued in U.S. Appl. No. 14/433,431.
Satomi Chiken and Atsushi Nambu. "High Frequency Pallidal Stimulation Disrupts Information Flow Through the Allidum by Gabaergic Inhibition", The Journal of Neuroscience, p. 2268-2280, 2013.

* cited by examiner

Single stimulation

GPi: Inhibition

GPe: Inhibition+excitation

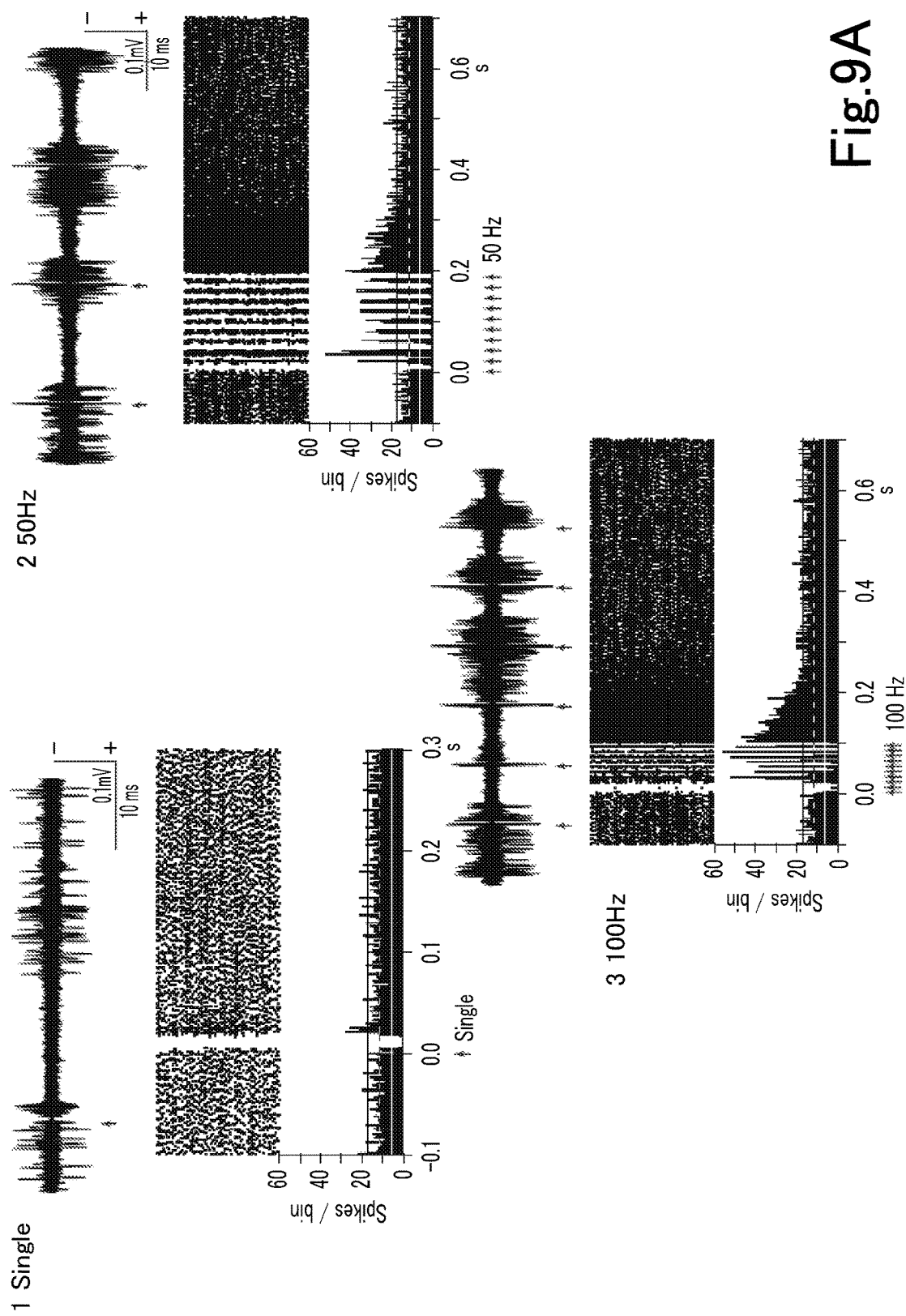

APPARATUS FOR ACQUIRING ELECTRIC ACTIVITY IN THE BRAIN AND UTILIZATION OF THE SAME

This is a continuation application of U.S. patent application Ser. No. 14/433,431 filed on Apr. 3, 2015, which is a National Phase Application of No. PCT/JP2013/077107 filed Oct. 4, 2013, which claims the benefit of Japanese Application No. 2012-223564 filed Oct. 5, 2012. The disclosure of the prior applications are hereby incorporated by reference herein in their entirety.

TECHNICAL FIELD

The present specification refers to apparatus for acquiring an electric activity and utilization of the apparatus for acquiring electric activity.

DESCRIPTION OF RELATED ART

Conventionally, treatments targeted at a particular site of the brain in a human being or the like have been carried out, and using monkeys and the like, studies on an electric activity of the particular site of the brain have also been conducted.

Stereotactic surgery is one of treatment approaches for human patients. The stereotactic surgery is applied to basal ganglia dysfunctions such as Parkinson's disease and dystonia. An example of the stereotaxy is a treatment of destroying nerve cells in an abnormally firing site by thermocoagulation or burying an electrode for applying an electric stimulation so as to allow for an appropriate activity (deep brain stimulation (DBS)).

During the stereotactic surgery in which a particular nucleus in the brain is a target site, normally, the target site is roughly identified by MRI or the like, a skull is removed with an excised diameter of approximately 2 cm under local anesthesia, and a needle like component with a recording electrode is slowly inserted through an opening to a site expected to be the target site. During the insertion, spontaneous neural activities of the insertion site is recorded through the recording electrode or neural activities related to movement of upper and lower extremities which are associated with sensory input are recoded, to determine whether or not the insertion site is the target site.

Furthermore, in the studies using monkeys and the like, a needle like component with a diameter of approximately 500 micrometers is used which includes a recording electrode at a tip portion of the needle like component and which can be inserted into the brain. Also for human patients, after such a recording electrode is used to identify the target site, a needle like component having a shape similar to the shape of the needle like component with the recording electrode and including a simulation electrode is inserted to apply the electric stimulation to the target site. Then, the appropriateness of the identification of the target site is checked using, as an indicator, symptom improvement or a side effect resulting from the electric stimulation.

Various electrodes buried in the stereotactic surgery have been provided. For example, an electrode apparatus has been disclosed which includes a needle-like metal electrode main body and a plurality of electrode groups provided on the electrode main body (Japanese Patent Application Laid-open No. 2011-36360). In the electrode apparatus, the potential of the expected target site is measured by a tip portion of the electrode main body. Furthermore, an electrode apparatus has been disclosed in which a large number of electrodes are provided on a surface of a base portion of the needle like component (Japanese Patent Application Laid-open No. 2007-325652).

CITATION LIST

Patent Literature

Patent Literature 1: Japanese Patent Application Laid-open No. 2011-36360
Patent Literature 2: Japanese Patent Application Laid-open No. 2007-325652

However, even the above-described needle-like electrode for studies only identifies the target site in the brain based on the spontaneous neural activity or sensory input. Therefore, the identification of the target site is often difficult, and the target site has not always been reliably identified. Furthermore, even when the target site is successfully detected by the recording electrode, installation of the stimulation electrode at the same site is not necessarily ensured. Thus, it has sometimes been difficult to detect symptom improvement or a side effect serving as an indicator indicating whether or not the insertion site is the target site when the electric stimulation is applied.

Furthermore, Japanese Patent Application Laid-open No. 2011-36360 and Japanese Patent Application Laid-open No. 2007-325652 disclose that the buried electrode used for the stereotactic surgery includes the plurality of electrodes and that one of the electrodes may be used as the recording electrode, whereas one of the electrodes may be used as the stimulation electrode. However, it is still difficult to identify the target site based on the spontaneous neural activity or sensory input using the recording electrode and to identify the target site using the electric stimulation.

As described above, at present, although the recording electrode measuring the spontaneous neural activity or sensory input and the stimulation electrode applying stimulation are available, no apparatus suitable for reliable identification of the target site in the brain is known.

BRIEF SUMMARY

An object of the present specification is to provide an apparatus for acquiring electric activity suitable for identification of the target site in the brain and utilization of the apparatus for acquiring electric activity.

The present inventors conducted various studies on the identification of the target site in the brain to obtain knowledge that, when the electric stimulation is applied to a site in the brain, the site exhibits a characteristic electric activity (discharge pattern). That is, the recording electrode is placed in the brain. The electric stimulation is applied through the stimulation electrode placed at or near the recording electrode. The electric activity induced by the stimulation is recorded through the recording electrode as the electric activity. The present inventors have obtained knowledge that the induced electric activity of this type is nucleus (in the brain)-specific, for the first time. Moreover, the present inventors have obtained knowledge that the above-described knowledge is used as an indicator in targeting a particular site in the brain, to allow the target site to be accurately and easily identified. Based on these pieces of knowledge, the present specification provides the following means.

(1) An apparatus for acquiring electric activity in the brain, comprising:
one or more needle-like bases enabled to be inserted into the brain;

a first electrode having a first impedance and enabling an input of an electric activity of a nucleus with which the first electrode comes into contact; and a second electrode having a second impedance lower than the first impedance and being able to output an electric stimulation to the nucleus, wherein the first electrode is provided at a tip portion of at least one of the one or more bases, and the second electrode is provided on a part of the at least one of the one or more bases at a position identical to a position of at least one of the first electrode or on a proximal side with respect to the first electrode, in a direction along a long axis of the base on which the first electrode is provided.

(2) The apparatus according to (1), wherein the apparatus is configured to receive, from the first electrode, the electric activity induced based on the electric stimulation output from the second electrode.

(3) The apparatus according to (1) or (2), wherein the second electrode is provided on the base provided with the first electrode at the tip portion.

(4) The apparatus according to any of (1) to (3), wherein the second electrode includes a pair of an anode and a cathode.

(5) The apparatus according to any of (1) to (4), wherein the second electrode is provided within a range in which the second electrodes; is placed in the same nucleus as the nucleus in which the first electrode is placed.

(6) The apparatus according to (5), wherein a distance between the first electrode and the second electrode along a long axis direction of the base provided with the first electrode is at most 200 micrometers.

(7) The apparatus according to (6), wherein the distance is at most 100 micrometers.

(8) The apparatus according to any of (1) to (7), wherein the one or more bases each comprise one or more terminals enabled to be connected to an output apparatus that outputs the electric stimulation from the second electrode and an input apparatus that acquires the electric activity induced by the electric stimulation and received from the first electrode.

(9) The apparatus according to any of (1) to (8), wherein the nucleus is one of a component nucleus of basal ganglia or a thalamus.

(10) The apparatus according to (9), wherein the component nucleus is one selected from the group consisting of an internal segment of a globus pallidus, an external segment of the globus pallidus, a putamen, a caudate nucleus, a ventral striatum, a ventral pallidum, a subthalamic nucleus, and a substantia nigra.

(11) An apparatus for identifying a target site in the brain, comprising:

one or more needle-like bases enabled to be inserted into the brain;

a first electrode having a first impedance and enabling an input of an electric activity of a possible target site with which the first electrode comes into contact; and a second electrode having a second impedance lower than the first impedance and being able to output an electric stimulation to the possible target sit; wherein the first electrode is provided at a tip portion of at least one of the one or more bases, and the second electrode is provided on a part of the at least one of the one or more bases at a position identical to a position of at least one of the first electrode or on a proximal side with respect to the first electrode, in a direction along a long axis of the base on which the first electrode is provided.

(12) The apparatus according to (11), where the apparatus identifies the target site by acquiring the electric activity which is induced based on the electric stimulation output from the second electrode and which is input from the first electrode.

(13) An apparatus for stimulating a target site in the brain, comprising:

one or more needle-like bases enabled to be inserted into the brain;

a first electrode having a first impedance and enabling an input of an electric activity of a contact site; and a second electrode having a second impedance lower than the first impedance and being able to output an electric stimulation to the contact site or a vicinity of the contact site, wherein the first electrode is provided at a tip portion of at least one of the one or more bases, and the second electrode is provided on a part of the at least one of the one or more bases at a position identical to a position of at least one of the first electrode or on a proximal side with respect to the first electrode, in a direction along a long axis of the base on which the first electrode is provided.

(14) The apparatus according to claim 13, wherein the apparatus identifies the target site by acquiring the electric activity which is induced based on the electric stimulation output from the second electrode and which is input from the first electrode, and outputs the electric stimulation to the target site from the second electrode.

(15) An apparatus improving or treating an electric activity of a target site in the brain, the apparatus comprising:

one or more needle-like bases enabled to be inserted into the brain;

a first electrode having a first impedance and enabling an input of an electric activity of a contact site; and a second electrode having a second impedance lower than the first impedance and being able to output an electric stimulation to the contact site or a vicinity of the contact site, wherein the first electrode is provided at a tip portion of at least one of the one or more bases, and the second electrode is provided on a part of the at least one of the one or more bases at a position identical to a position of at least one of the first electrode or on a proximal side with respect to the first electrode, in a direction along a long axis of the base on which the first electrode is provided.

(16) The apparatus according to (15), which identifies the target site by acquiring the electric activity which is induced based on the electric stimulation output from the second electrode and which is input from the first electrode, the apparatus outputting the electric stimulation to the target site through the second electrode.

(17) A system for recording an electric activity in the brain, comprising:

the apparatus for acquiring electric activity in the brain according to any of (1) to (10);

an output apparatus that outputs an electric stimulation from the second electrode;

an input apparatus that acquires the electric activity induced by the electric stimulation and recorded from the first electrode; and a control apparatus that determines whether or not an insertion site of the first electrode is a preset particular nucleus, based on the acquired electric activity and an electric activity characteristic of the particular nucleus.

(18) The system according to (17), wherein the output apparatus or the control apparatus controls a current value and/or a current waveform of the electric stimulation output from the second electrode.

(19) The system according to (17) or (18), further comprising a storage apparatus, the storage apparatus storing the electric activity characteristic of the preset particular nucleus.

(20) The system according to (19), wherein the storage apparatus stores the electric activity characteristic of the preset particular nucleus.

(21) The system according to any of (17) to (20), further comprising a display apparatus that displays the electric activity received from the first electrode.

(22) A method for operating a system for acquiring electric activity, the system including:
the apparatus for acquiring electric activity in the brain according to any of (1) to (10);
an output apparatus that outputs an electric stimulation, from the second electrode;
an input apparatus that acquires the electric activity induced by the electric stimulation and recorded from the first electrode; and
a control apparatus,
the method comprising:
the output apparatus outputting the electric stimulation to an insertion site of the first electrode or a vicinity of the insertion site from the second electrode, and
the input apparatus acquiring the electric activity induced by the electric stimulation and recorded from the first electrode.

(23) A method for improving or treating an electric activity of a target site in the brain, the method, in use of the apparatus for acquiring electric activity according to any of (1) to (10), the apparatus executing:
a step of identifying the target site by acquiring the electric activity which is induced based on the electric stimulation output from the second electrode and which is input from the first electrode; and
a step of outputting the electric stimulation to the target site by the second electrode.

BRIEF DESCRIPTION OF DRAWINGS

FIG. 9A is a diagram showing the electric activity induced by the application of the single stimulation and the repetitive stimulation to the external segment of the globus pallidus.

DETAILED DESCRIPTION

A disclosure herein relates to an apparatus for acquiring electric activity in the brain and utilization of the apparatus. The present specification is based on following new knowledge. The present inventors has obtained knowledge that, when electric stimulation is applied through a recording electrode placed in the brain and a stimulation electrode placed at the same position as that of the recording electrode or near the recording electrode, the brain site-specific electric activity is recorded through the recording electrode. A summary of the knowledge is shown in FIG. 1.

Figure 1:
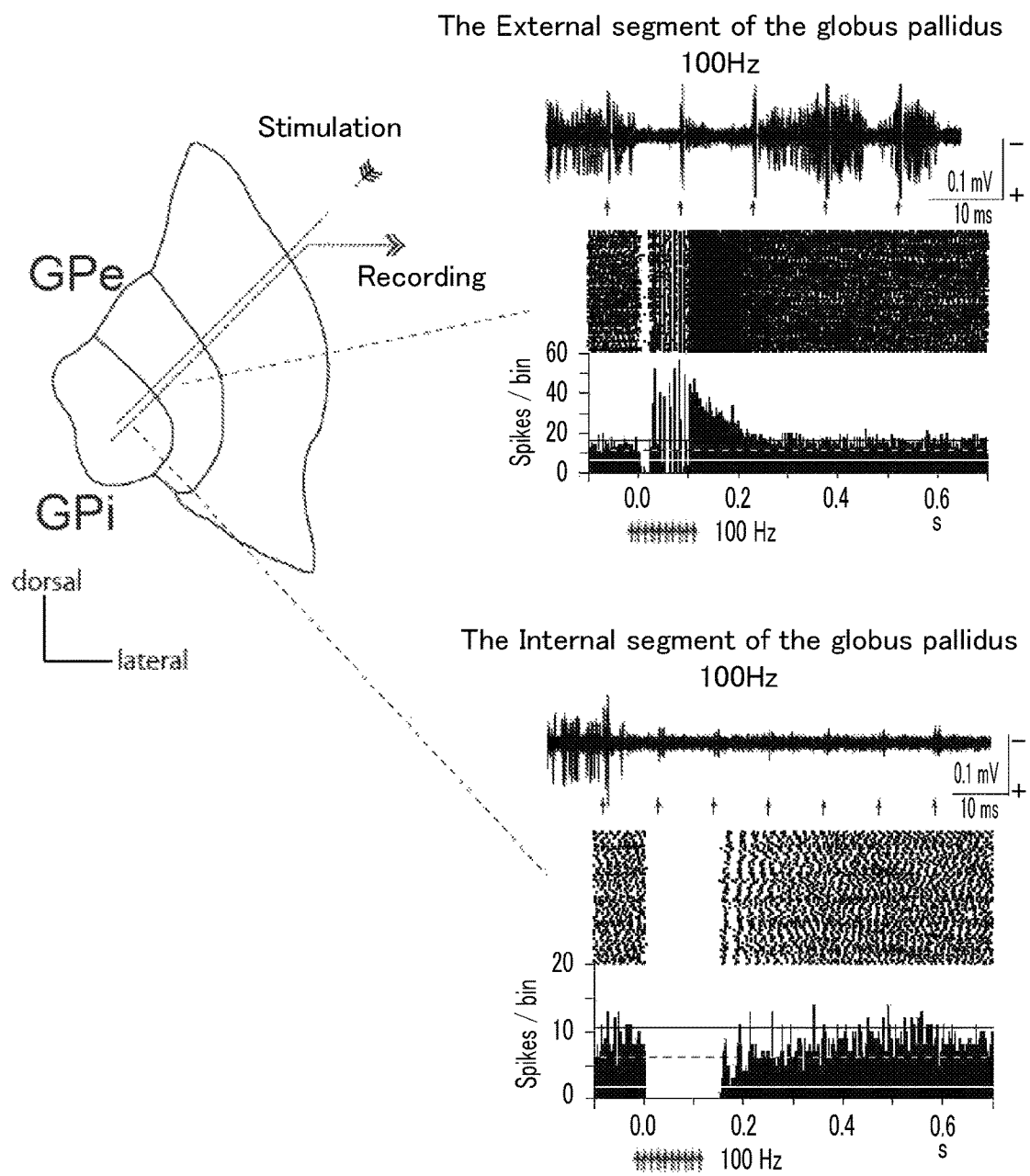
FIG. 1 is a diagram showing an example of component nuclei of the basal ganglia and a specific electric activity.
Figure 4:
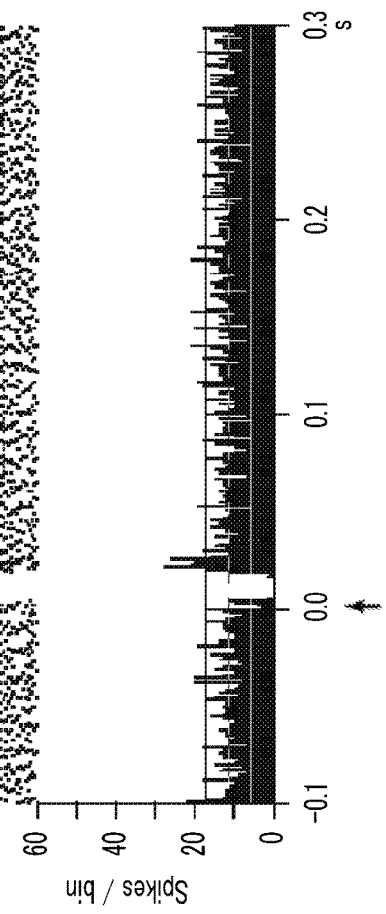
FIG. 4 is a diagram showing an example of an apparatus for acquiring electric activity induced when single stimulation is applied to the internal segment and the external segment of the globus pallidus.
Figure 4:
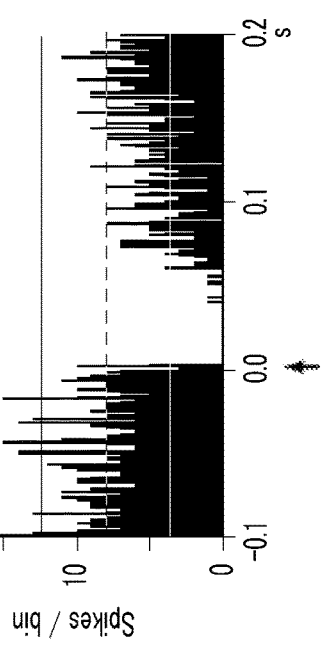
Figure 5:
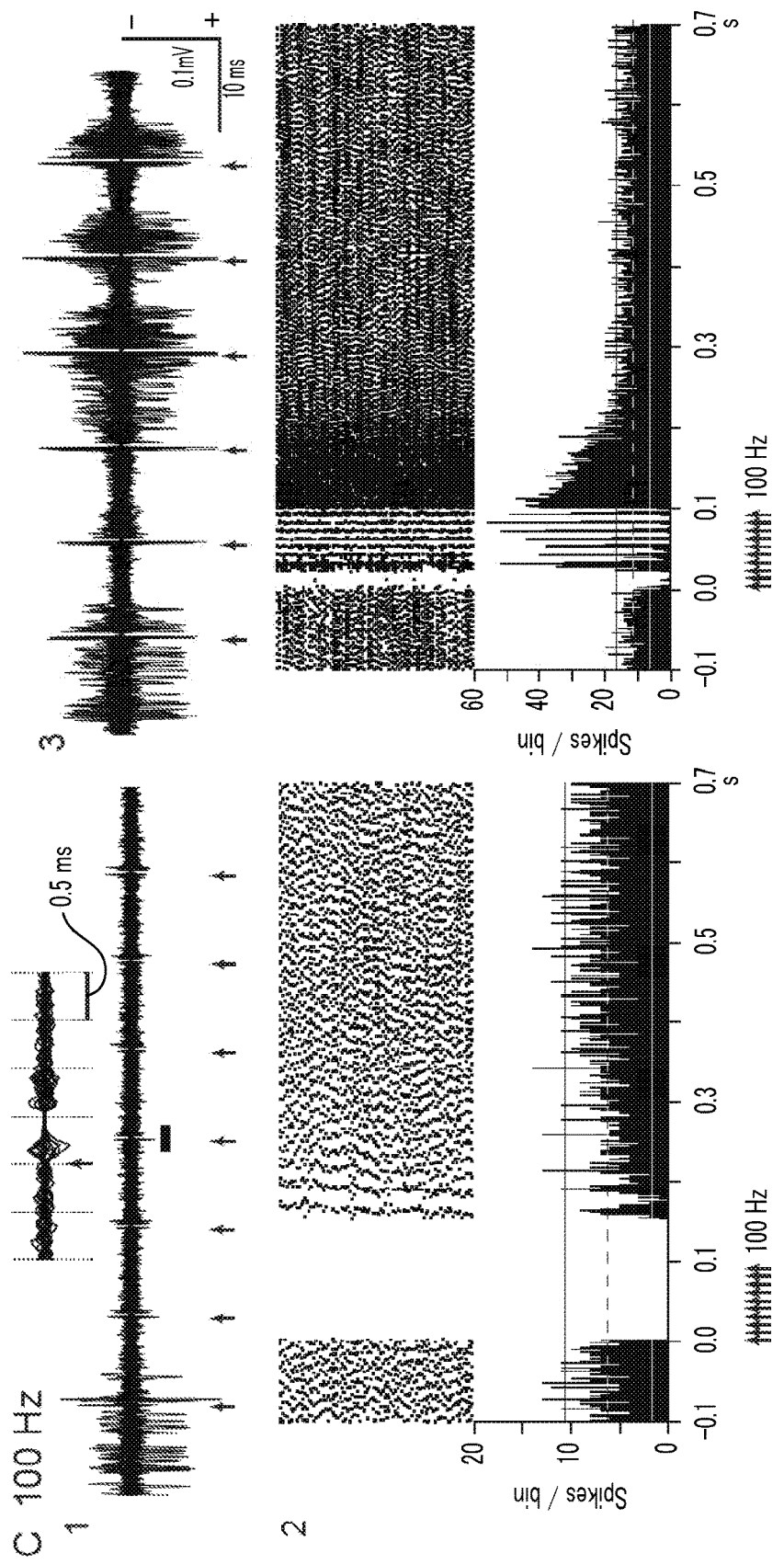
FIG. 5 is a diagram showing an example of the electric activity induced when repetitive stimulation is applied to the internal segment and the external segment of the globus pallidus.

As shown in FIG. 1, the recording electrode and the stimulation electrode are introduced into a particular nucleus in the brain, and a current with a predetermined current value and a predetermined waveform is output from the stimulation electrode. Then, the particular electric activity is recorded according to the brain site. Regardless of whether the applied electric stimulation is single stimulation or repetitive stimulation, the specific electric activity can be acquired as shown in FIG. 4 and FIG. 5. The specific electric activity is observed using a voltage waveform (raw waveform) based on action potential and raster displays or histograms based on the action potential. The present inventors examined various sites in the brain to come to a conclusion that the induced electric activity of this type is brain site-specific.

The apparatus for acquiring electric activity disclosed herein includes a first electrode having a first impedance and to which an electric activity of a nucleus with which the first electrode comes into contact is enabled to be input, and a second electrode having a second impedance lower than the first impedance and which is enabled to output an electric stimulation to the nucleus or a vicinity thereof. Moreover, the first electrode is provided at a tip portion of at least one of the one or more bases, and the second electrode is provided on a part of the at least one of the one or more bases at a position identical to a position of at least one of the first electrode or on a proximal side with respect to the first electrode, in a direction along a long axis of the base on which the first electrode is provided. Adoption of this configuration allows the electric stimulation to be applied to the nucleus with which the first electrode comes into contact or to the vicinity of the nucleus so that a nucleus-specific electric activity induced by the electric stimulation is input to the first electrode. Thus, the present apparatus can acquire the nucleus-specific electric activity induced by the electric stimulation.

Furthermore, the present apparatus can search for the nucleus-specific electric activity, a disease-specific electric activity, or an individual-specific electric activity in the brain.

Moreover, the present apparatus may be used not only to acquire the electric activity but also to identify a target site. This is because the brain site-specific electric activity can be used to determine whether or not art insertion site of the first electrode is the intended target site. The acquired electric activity is compared with a pre-acquired brain site-specific electric activity to enable easy and reproducible determination of whether or not the insertion site of the first electrode is the intended brain site.

Moreover, the present apparatus can apply the electric stimulation to the target site. When the target site is identified by the first electrode, the second electrode can output a stimulation current to the target site because the second electrode is arranged at or near the first electrode. Output of the stimulation current allows symptom improvement or exertion of a side effect to be checked for, enabling check of whether or not the first electrode position is the target site. Furthermore, the second electrode outputs a stimulation current for treatment to improve the electric activity of the target site, thus allowing an associated disease to be improved and treated.

A system including, besides the present apparatus, an output apparatus that can output the electric stimulation from the second electrode, an input apparatus to which the electric activity from the first electrode can be input, and a control apparatus that makes determination on the acquired electric activity may be used to acquire the electric activity of the nucleus, search for the nucleus-specific electric activity, identity the target site, apply electric stimulation to the target site, and improve and treat the electric activity of the target site.

Typical and non-limiting specific examples of the disclosures of the Description are explained in detail below with reference to the drawings. These detailed explanations are aimed simply at showing preferred examples of the disclosures of the Description in detail so that they can be implemented by a person skilled in the art, and are not intended to limit the scope of the disclosures of the Description. The additional features and disclosures disclosed below may be used separately or together with other features and teachings to provide a further improved apparatus for acquiring electric activity in brain or the like.

The combinations of features and steps disclosed in the detailed explanations below are not essential for implementing the disclosures of the Description in the broadest sense, and are presented only for purposes of explaining typical examples of the disclosures of the Description in particular. Moreover, the various features of the typical examples above and below and the various features described in the independent and dependent claims do not have to be combined in the same way as in the specific examples described here, or in the listed order, when providing addition useful embodiments of the disclosures of the Description.

All features described in the Description and/or Claims are intended as individual and independent disclosures restricting the initial disclosures and the claimed matter specifying the teaching, separately from the constitution of features described in the Examples and/or Claims. Moreover, all descriptions of numerical ranges and groups or sets are intended to include intermediate configurations for purposes of restricting the initial disclosures and the claimed matter specifying the teaching.

(Apparatus for Acquiring Electric Activity in the Brain and the System with the Apparatus)

Figure 2:
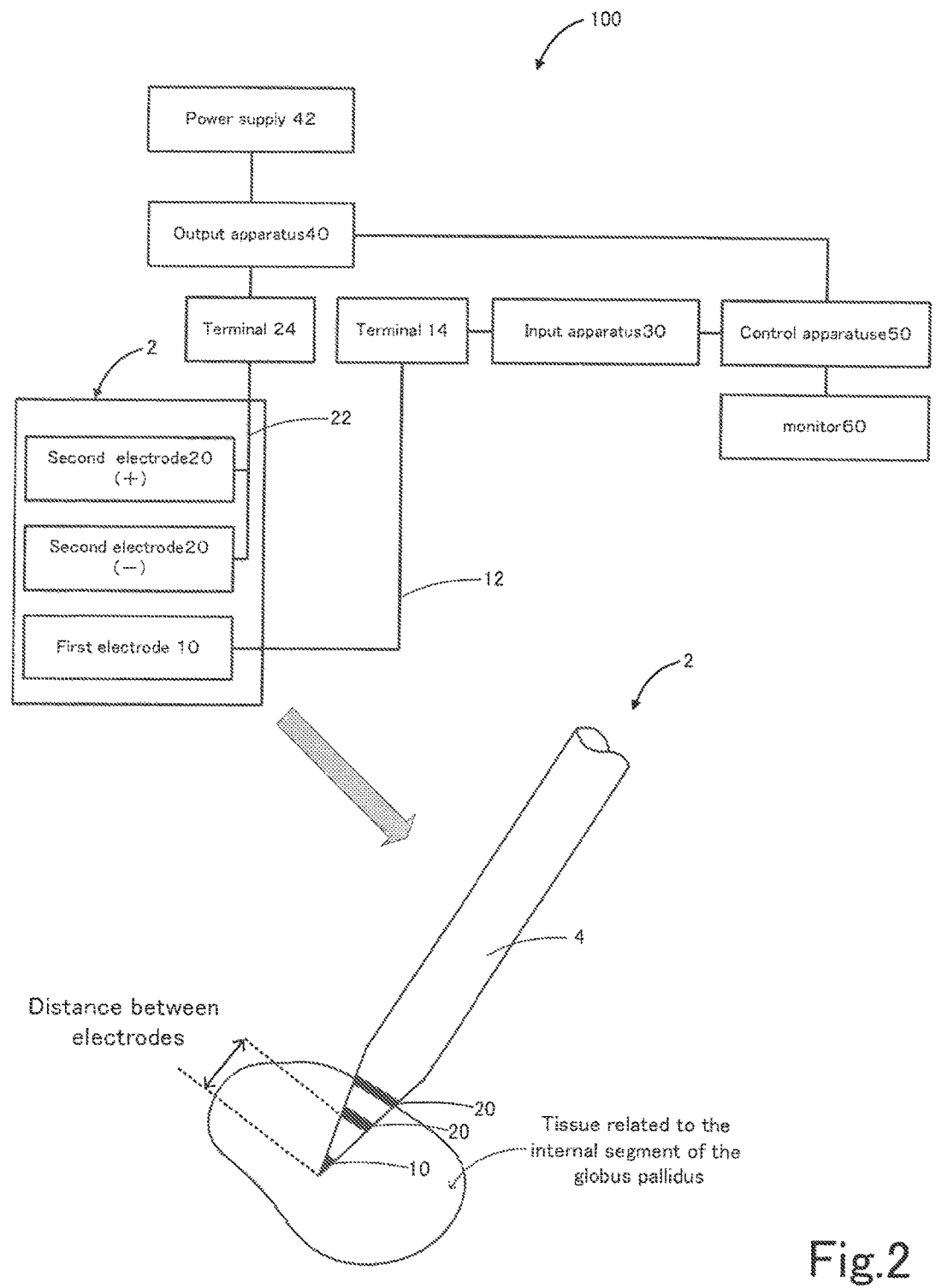
FIG. 2 is a diagram showing an example of an apparatus for acquiring electric activity and a system disclosed herein.

FIG. 2 shows a form of an apparatus for acquiring electric activity 2 disclosed herein and a system 100 including the apparatus for acquiring electric activity 2. As shown in FIG. 2, the apparatus for acquiring electric activity 2 may include one or more needle-like bases 4 that may be inserted into the brain, a first electrode 10 having a first impedance and to which the electric activity of the nucleus with which the first electrode 10 comes into contact may be input, and a second electrode 20 having a second impedance lower than the first impedance and which may output the electric stimulation to the nucleus.

(Base)

The base 4 is shaped like a needle that can be inserted into the brain. The base 4 is not particularly limited as long as the base 4 may be inserted into the brain 4. The base 4 may be shaped like a rod or a band, and a cross-sectional shape of the base 4 is not particularly limited. A length of a portion of the base 4, which is inserted and placed in the brain, is normally about 80 mm to 160 mm. Furthermore, when the base 4 is, for example, circular in cross section, the base 4 is approximately 300 micrometers to approximately 1,000 micrometers.

A tip of the base 4 is preferably more pointed than a proximal side so as to be easily inserted into the brain. Typically, examples of the shape include a cone and a truncated cone. For example, the diameter at a vicinity of the tip portion may be at least approximately 5 micrometers and at most approximately 100 micrometers.

One base 4 may be provided or two or more bases 4 may be provided. When the two or more bases 4 are provided, for example, one first electrode described below may be provided at the tip portion of one of the bases 4, and another first electrode 10 may be provided at the tip portion of another of the bases 4. Furthermore, the second electrode 20 described below may also be provided on a part of the base 4. When the two or more bases 4 are provided, the plurality of bases 4 is preferably integrated each other so as to be bundled along a long axis direction of the bases 4. Additionally, when the two or more bases 4 are used, the bases 4 are preferably configured to move relative to one another or such that one of the bases 4 moves along the long axis direction relative to another of the bases 4, so as to enable adjustment of an inter-electrode distance between the first electrode 10 and the second electrode 20 or positions of the first electrode 10 and the second electrode 20.

A material for the base 4 is not particularly limited, and any of well-known materials used for insertion into the brain may be selected and used as needed. For example, a material is used which is strong or rigid enough to be inserted into the brain and which itself has an insulating property, is non-toxic to living organisms, and does not react with the living organisms. Alternatively, for example, a conductive material with such an appropriate rigidity may be coated with an insulating material or the like.

(First Electrode)

The first electrode 10 has the first impedance and is configured such that the electric activity of the nucleus with which the first electrode 10 comes into contact can be input. The first impedance of the first electrode 10 is preferably configured to fall within a range suitable for recording the electric activity of the nucleus or cells in the brain with which the first electrode 10 comes into contact. This is to eliminate noise to record the electric activity of a single nerve cell or a plurality of nerve cells as well as possible. The first impedance is determined from the above-described perspectives. The first impedance is also determined in accordance with a type of the intended nucleus or cells in the brain and a type of the electric activity to be input, as needed.

The first impedance may be at least approximately 0.6 megaohms and at most approximately 1.5 megaohms when measured at 1 kHz. Within this range, the electric activity of the single nerve cell or the plurality of nerve cells in a limited area in a nerve nucleus can be effectively recorded. To acquire the above-described first impedance, it is effective to use a material with appropriate resistance to reduce an electrode area. Examples of a material for the above-described first electrode 10 include Elgiloy, tungsten, and platinum iridium. In the specification, the impedance is measured at a frequency of 1 kHz and at a temperature of at least 20 degrees centigrade and at most 40 degrees centigrade and preferably at a temperature close to a body temperature of mammals, more specifically, at least 30 degrees centigrade and at most 40 degrees centigrade.

The first electrode 10 may be provided at the tip portion of the base 4, and a form of the first electrode 10 is not particularly limited. The first electrode 10 may provide a pointed tip portion of the base 4 formed of an insulating material. Furthermore, the first electrode 10 may be configured to cover at least a part of the pointed tip portion of the base 4 formed of the insulating material.

Figure 3:
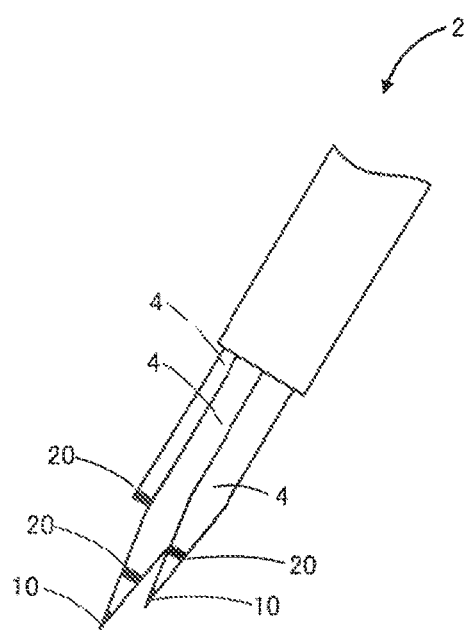
FIG. 3 is a diagram showing another example of the apparatus for acquiring electric activity disclosed herein.

As shown in FIG. 2, the at least one first electrode 10 may be provided at the tip portion of the one base 4. For example, as shown in. FIG. 3, the two or more first electrodes 10 may be provided at the respective tip portions of the bundled different bases 4 as needed. For example, the first electrodes 10 may be prepared for different positions (different depths), different impedances, or the like so that the different first electrode 10 is used as a recording (input) electrode as needed.

The first electrode 10 can be connected to an input apparatus 30 to which the electric activity of the nucleus or cells with which the first electrode 10 comes into contact is input. That is, wiring 12 that can be connected to the input apparatus 30 is connected to the first electrode 10. For example, as shown in FIG. 2, an end of the wiring 12 that is different from an end of the wiring 12 connected to the first electrode 10 is connected to the input apparatus 30 via an appropriate 110 terminal 14. The input apparatus 30 is an apparatus that acquires the electric activity input by the first electrode. The wiring 12 is appropriately arranged with respect to the base 4. Disposition of the wiring 12 may be determined by those skilled in the art according to a shape of the base 4 or the like as needed. The terminal 14 and the input apparatus 30 can be connected together using an appropriate plug including the wiring extending from the input apparatus 30.

(Second Electrode)

The second electrode 20 has the second impedance and is formed to be able to output the electric stimulation to the nucleus or cells with which the first electrode 10 comes into contact. The second impedance of the second electrode 20 is set lower than the first impedance of the first electrode 10 so as to be suitable for application of the electric stimulation. The second impedance is also determined depending on the intended nucleus or cells in the brain or the type of the electric stimulation to be output, as needed.

The second impedance is not particularly limited but may be, for example, at least approximately 10 kiloohms and at most approximately 500 kiloohms as measured at 1 kHz. This is because this range allows a sufficient amount of current to be passed with an applied voltage of approximately 100 V. To acquire the above-described second impedance, it is effective to increase the electrode area or use a material with an appropriate resistance. Examples of a material for the above-described second electrode 20 include Elgiloy, tungsten, platinum, and stainless steel.

The second electrode 20 is provided on the base 4 at a position identical to the position of the first electrode 10 or on a proximal side with respect to the first electrode 10 in a direction along a long axis of the base 4 on which the first electrode 10 is provided. Thus, application of the electric stimulation through the second electrode 20 allows input of the nucleus-specific electric activity through the first electrode 10.

As shown in FIG. 2, the second electrode 20 may be provided at the tip portion of the base 4 itself provided with the first electrode 10 at the tip portion thereof or on the proximal side with respect to the tip portion. Then, the single base 4 is provided with the first electrode 10 and the second electrode 20, allowing the apparatus to be made less invasive.

Furthermore, as shown in FIG. 3, the second electrode 20 may be provided at the tip portion of the base 4 that is different from the base 4 provided with the first electrode 10 at the tip portion thereof. Then, a combination of the first electrode 10 and the second electrode 20 can be acquired using the simple configuration. Moreover, when a plurality of the bases 4 is configured to be movable relative to one another along the long axis direction of the bases 4, a distance between the fast electrode 10 and the second electrode 20 can be easily adjusted.

Furthermore, regardless of whether the second electrode 20 is provided on the base 4 that is provided with the first electrode 10 or on the base 4 that differs from the base 4 that is provided with the first electrode 10, the second electrode 20 may be provided which is arranged at a different distance from the first electrode 10. Then, selection of the second electrode 20 for use as needed allows acquisition of the electric activity in a case with the different distance between the first electrode 10 and the second electrode 20.

When provided on the base 4 with the first electrode 10, the second electrode 20 is provided on the proximal side with respect to the tip portion of the base 4. When provided on the base 4 different from the base 4 that is provided with the first electrode 10, the second electrode 20 may be provided at the tip portion of the different base 4 or on the proximal side.

The second electrode 20 may be provided on the base 4 in any form, for example, as long as the second electrode 20 is formed to output the electric stimulation to the nucleus or cells with which the first electrode 10 comes into contact or to the vicinity of the nucleus or cells. For example, the second electrode 20 may be provided like a ring around the base 4 as shown in FIG. 2. Furthermore, the second electrode 20 may be provided like a band corresponding to an incomplete ring. Moreover, the second electrode 20 may be applied to a surface of the base 4 in an electrode pattern in an appropriate two- or three-dimensional form.

The position of the second electrode 20 with respect to the first electrode 10 is not particularly limited. For example, when the first electrode 10 is placed at a certain component nucleus of basal ganglia, the second electrode 20 may be provided at such a position (distance) where the second electrode 20 is arranged at another component nucleus. For example, when the first electrode 10 is positioned at the internal segment of the globus pallidus, the second electrode 20 may also be provided at such a position (in such an arrangement) where the second electrode 20 is also positioned at the internal segment of the globus pallidus. Alternatively, the second electrode 20 may be provided at any position other than the internal segment of the globus pallidus, for example, at the external segment of the globus pallidus or at another component nucleus. A positional relation between the first electrode 10 and the second electrode 20 is determined as needed.

Preferably, as shown in FIG. 2, the second electrode 20 is provided in the same nucleus as that in which the first electrode 10 is positioned. Acquisition of the electric activity induced by application of the electric stimulation to the same nucleus or cells allows the nucleus-specific electric activity to be easily acquired.

Such a distance between the first electrode 10 and the second electrode 20 varies according to a pattern of the applied electric stimulation, a type of the target nucleus, or a type or age of an individual. An appropriate distance can be determined by evaluating the distance between the first electrode 10 and the second electrode 20 and a tendency of acquisition of the electric activity induced by the electric stimulation. Typically, the distance between the first electrode 10 and the second electrode 20 along the long axis direction of the base 4 with the first electrode 10 may be at most appropriately 200 micrometers. This is because this range allows the first electrode 10 and the second electrode 20 to be placed in the same nucleus in many cases, and also enables the first electrode 10 to effectively detect the electric activity induced by the electric stimulation output from the second electrode 20. More preferably, the distance is at most 100 micrometers. Additionally, the distance is at least 0 micrometers, but preferably at least 10 micrometers and more preferably at least 20 micrometers.

The second electrode 20 may be provided as an electrode (cathode) paired with an electrode (anode) present on a patient's body surface or in another site in the patient's body. However, as shown in FIG. 2, the second electrode 20 preferably includes two electrodes corresponding to a pair of an anode and a cathode. This allows the predetermined electric stimulation to be reliably applied to the vicinity of the first electrode 10. An arrangement form of the second electrode 20 with the pair of the anode and the cathode is not particularly limited. In FIG. 2, the cathode and the anode are arranged in this order from the tip side along the long axis direction of the base 4. However, the embodiment is not limited to this arrangement. A distance between the anode and the cathode of the pair of the anode and the cathode of the second electrode 20 is not particularly limited. However, the distance may be set to at least approximately 300 micrometers and at most approximately 1,000 micrometers and more preferably to at least approximately 400 micrometers and at most approximately 600 micrometers in order to allow the localized target to be sufficiently stimulated.

An output apparatus 40 that allows the second electrode 20 to output the electric stimulation is connected to the second electrode 20. Wiring 22 that can be connected to the output apparatus 40 is connected to the second electrode 20. For example, as shown in FIG. 2, an opposite end of the wiring 22 to an end thereof connected to the second electrode 20 is connected to the output apparatus 40 via an appropriate 110 terminal 24. The wiring 22 is appropriately arranged with respect to the base 4. Disposition of the wiring 22 may be determined by those skilled in the art according to the shape of the base 4 or the tike as needed. The terminal 24 and the output apparatus 40 can be connected together using an appropriate plug including the wiring extending from the output apparatus 40.

A system for acquiring electric activity including the apparatus 2 will be described below. The system 100 includes, besides the apparatus 2, the input apparatus 30, the output apparatus 40, a control apparatus 50, and a monitor 60.

(Output Apparatus)

The output apparatus 40 receives a supply of electricity from a power supply 42 provided in or outside the output apparatus 40 and can convert the electricity such that the electricity has an appropriate current value or waveform and supply the resultant electricity to the second electrode 20. A predetermined current output by the output apparatus 40 may be intended to apply the electric stimulation for allowing the first electrode 10 to acquire the nucleus-specific electric activity or to confirm that the nucleus with which the first electrode 10 comes into contact is the target site. Control of the current value and the waveform in the output apparatus 40 is performed by the control apparatus 50 described below.

(Input Apparatus)

The input apparatus 30 can appropriately acquire and amplify the electric activity received from the first electrode 10. Analysis of a current acquired from the first electrode 10 is performed by the control apparatus 50.

(Control Apparatus)

The control apparatus 50 is configured as a normal computer and includes a hard disk and a RAM besides a CPU. The control apparatus 50 executes a control program held in the hard disk to transmit a control signal to the output apparatus 40 to output the predetermined current value and waveform through the second electrode 20. Furthermore, the control apparatus 50 executes the control program held in the hard disk to process the current value and waveform of the electric activity acquired from the first electrode 10 to acquire information on the electric activity, and stores the information in the hard disk and also outputs the information to the monitor 60.

Moreover, the control apparatus 50 holds, in the hard disk, the pre-acquired nucleus specific electric activity (combination of applied electric stimulation and induced electric activity) (current value and waveform). The control apparatus 50 executes the control program held in the hard disk to compare the newly acquired electric activity with the pro-acquired nucleus-specific electric activity to identify the nucleus or the target site.

Now, use of the system 100 shown in FIG. 2 will be described. First, before utilization of the system 100, the base 4 is inserted toward the target site in the basal ganglia (in this case, the internal segment of the globus pallidus). Before the insertion, normally, a frame is installed on the skull and MRI is preformed to roughly identify the target site. Furthermore, an insertion direction of the base 4 is determined. Then, under local anesthesia, the skull in a frontal part of a head is excised with an excised diameter of approximately 2 cm, and the base 2 is slowly inserted through au opening toward the target site. Such an insertion process for the base 2 may be executed automatically or by a robot.

Once the base 4 has been inserted to some degree, the control apparatus 50 transmits the control signal to the output apparatus 40 to allow the output apparatus 40 to output, through the second electrode 20, predetermined electric stimulation suitable for identification of the target site. Upon receiving the signal, the output apparatus 40 converts the current from the power supply 42 into the predetermined electric stimulation and supplies the electric stimulation to the second electrode 20 to allow the second electrode 20 to output a predetermined stimulation current. The control apparatus 50 acquires, via the input apparatus 30, the induced reaction received from the first electrode 10, records the induced reaction in one or more types of desired forms selected from raw waveforms, raster displays, and histograms, and also allows the monitor 60 to display the induced reaction. The above-described procedure is repeated with the base 2 inserted little by little until the first electrode 10 at the tip portion reaches and then passes through a site expected to be the insertion target site.

The electric stimulation output from the second electrode 20 may be single stimulation as shown in FIG. 4. For the single stimulation, for example, when the target site is the internal segment of the globus pallidus, inhibition for a given period of time follows the stimulation (left figure). Furthermore, when the target site is the external segment of the globus pallidus, excitation follows the inhibition for the given period of time (right figure). As shown in FIG. 5, the electric stimulation may be repetitive stimulation. For the repetitive stimulation, the electric activity induced by the single stimulation is emphasized, preferably leading to a tendency of specificity to become noticeable. As shown in FIG. 5, application of the repetitive stimulation to the internal segment of the globus pallidus results in an extended inhibition period (left figure). Additionally, when the repetitive stimulation is applied to the external segment of the globus pallidus, inhibition and excitation occur repeatedly each time the stimulation is applied, and strong excitation follows end of the stimulation (right figure).

The electric stimulation is normally provided by specifying the current value and the waveform. Thus, various stimulation patterns may be configured both in the single stimulation and in the repetitive stimulation. For the electric stimulation, only the single stimulation, only the repetitive stimulation, or a combination of the single stimulation and the repetitive stimulation may be applied. A plurality of types of the electric stimulation (a plurality of types of single stimulation, a plurality of types of repetitive stimulation, and both single stimulation and repetitive stimulation) are combined together to allow a more specific and more accurate electric activity to be obtained.

The above-described information on the nucleus-specific electric activity is pre-acquired to allow the nucleus with which the first electrode 10 comes into contact to be easily discriminated from the adjacent tissues for identification described below.

For example, as described above, the internal segment and the external segment of the globus pallidus are easily identified by the single stimulation and/or the repetitive stimulation using apparatus 2 for acquiring the electric activity.

When the predetermined stimulation current is output from the second electrode 20, the nucleus-specific electric activity occurs in the nucleus or a vicinity thereof, and an induced current corresponding to the electric activity is input to the first electrode 10. The input apparatus 30 amplifies an input slight potential and outputs the amplified potential to the control apparatus 50. The control apparatus 50 stores the potential as new electric activity information and also displays the information on the monitor 60. A form of the display is selected from raw waveforms, raster displays, and histograms as needed.

The above-described process allows the present system 100 to acquire the information on the nucleus-specific electric activity induced by the electric stimulation. The system can also acquire new information on the nucleus-specific electric activity, a disease-specific electric activity, or an individual-specific electric activity.

The system 100 can also execute the following process. The control apparatus 50 compares the saved electric activity information on one or more target sites with the acquired electric activity information to determine whether or not the first electrode 10 at the tip portion of the base 4 is positioned at the target site. This process allows the target site to be identified, Identification of the target site (diseased site) is conventionally difficult to achieve only with spontaneous electric activity. However, the present system 100 performs comparison with the nucleus-specific electric activity information to achieve easy and accurate identification of the target site.

The present system 100 can further execute the following process, Upon successfully determining that the position of the first electrode 10 is the target site, the control apparatus 50 outputs the control signal to the output apparatus 40 to allow the output apparatus 40 to output the predetermined stimulation current through the second electrode 20. When an effect of the output of the stimulation current from the second electrode 20 such as improvement of a symptom of the individual is confirmed, the site with which the first electrode 10 is in contact can be determined to be the target site. This enables more accurate identification. Furthermore, if a side effect results from the stimulation, the target site can be determined to be inappropriate.

On the other hand, upon failing to affirmatively determine that the position of the first electrode 10 is the target site, the control apparatus 50 can display a message "not the target site" on the monitor 60 and also instruct the robot to change the insertion position of the base 2 (to insert the base 2 more deeply or shallowly). The above-described identification process is repeated to allow the target site to be accurately determined.

As described above, the present system 100 can easily acquire the information on the electric activity of the nucleus in the brain, more specifically, the information on the electric activity induced by the electric stimulation. The present system 100 can then acquire or search for the information on the nucleus-specific electric activity in the brain for each individual, each nucleus, or each disease.

Moreover, since the information on the nucleus-specific electric activity can be acquired, the present system 100 enables the nucleus where the first electrode 10 is positioned to be identified as the particular nucleus or the target site based on the pre-acquired information on the specific electric activity associated with the nucleus, the disease, and the like.

Moreover, the present system 100 can supply the electric stimulation to the particular nucleus or the target site. Thus, the identified site can be easily rechecked, allowing identification accuracy to be increased.

The present system is effective for acquiring and searching for the electric activity in the brain and identifying and stimulating the target site. The site in the brain is not particularly limited, but the present system is preferably applied to the brain deep part, which is conventionally considered to be difficult to identify, that is, each component nucleus of the basal ganglia. Furthermore, the present system is preferable for stereotactic surgery for basal ganglia dysfunctions such as Parkinson's disease and dystonia. Specifically, the site may be the internal segment of the globus pallidus, the external segment of the globus pallidus, the subthalamic nucleus, the putamen, the caudate nucleus, the ventral striatum, the ventral pallidum, or the like. These component nuclei of the basal ganglion are related to basal ganglia dysfunctions such as Parkinson's disease, Huntington's disease, and dystonia, psychiatric disorders such as depression and obsessive-compulsive disorder, drug dependence, and the like. The present system is effective for improvement and treatment of these diseases.

The above-described apparatus 2 and system 100 are examples of the apparatus and system disclosed herein, and the present teaching is not limited to the apparatus 2 and the system 100. Conventionally known various forms are applicable to the configurations of the apparatus 2 and the system 100. The control apparatus including the CPU and a recording apparatus need not be a common computer but may be a small-sized chip.

In the system 100, the control apparatus 50 is provided independently of the output apparatus 40 and the input apparatus 30. However, the present teaching is not limited to this. The control apparatus 50 may be configured as two or more apparatuses. Some functions of the control apparatus 50 may be provided in the output apparatus 40, whereas other functions of the control apparatus 50 may be provided in the input apparatus 30.

In the above-described system 100, the output apparatus 40 is installed outside a patient's body. However, the present teaching is not limited to this. For example, the output apparatus 40 may be installed inside the patient's body or on the patient's body surface so that such a stimulation current as improves the symptom as needed is output to the target site through the second electrode 20. Then, the present apparatus 2 and system 100 can be utilized as a disease improvement or treatment apparatus or system.

The stimulation current with the current value and waveform suitable for disease improvement or treatment is well known to those skilled in the art and can be acquired for each disease or each individual as needed.

When the apparatus 2 and the system 100 are intended to improve or treat the disease or the like, the input apparatus 30 may be removed from the system 100 after the identification of the target site or provided on the patients body surface or inside the patients body similarly to the output apparatus 40. Likewise, the control apparatus 50 may be built into the input apparatus 30 or the output apparatus 40 or made compact. Moreover, the input apparatus 30 or the output apparatus 40 may be configured to be activated in accordance with a wireless signal from an external apparatus (control apparatus 50 or the like).

Moreover, in the apparatus 2 and the system 100, the base 4 may include a tube through which a particular drug can be injected. That is, the tube is provided along the long axis direction of the base 4, and the drug is injected to the identified target site through the tube. Then, an effect of the drug on the particular site can be easily checked, and introduction of the drug into the particular site is facilitated. The above-described apparatus 2 and system 100 are effective when the improvement or treatment of the disease in the brain is intended.

Furthermore, in the apparatus 2 and the system 100, the base 4 may include a member such as an electrode that enables a nucleus to be solidified or cauterized, That is, the electrode for solidification or cauterization is provided along the long axis direction of the base 4. Then, the nucleus in the identified target site can be easily destroyed. The above-described apparatus 2 and system 100 are effective when the improvement or treatment of the disease in the brain is intended.

In the above-described embodiment, the disclosure herein has been described in connection with the apparatus 2 and the system 100. However, the above-described embodiment may be implemented as usage of the apparatus or the system, and a method for operating the apparatus or the system and a method for controlling the apparatus or the system. That is, the above-described embodiment may be implemented as a method for acquiring the electric activity using the present apparatus or the present system, a method for applying the electric stimulation, a method for identifying the target site, a method for searching for the specific electric activity, a method for improving or treating the electric activity in the brain (method for preventing or treating the brain-related disease), and a method for operating or controlling the present apparatus or the present system which method is intended for a purpose similar to the purpose of each of the above-described methods.

The above-described embodiment is applicable to human beings and non-human-being primates and other experimental animals. The disclosure herein is used in order to improve or treat psychiatric and neurological diseases, and for the experimental animals, used for studies as well as for improvement or treatment of psychiatric and neurological diseases.

Example

The present teaching will be specifically described with reference to an example. However, the following example does not limit the present teaching.

Figure 6:
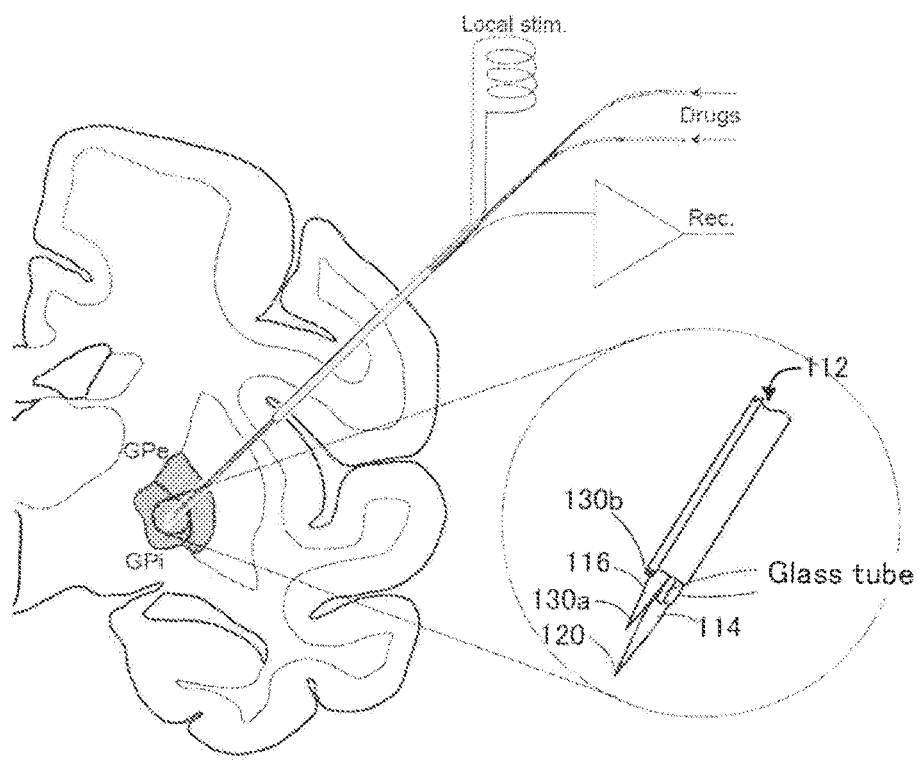
FIG. 6 is a diagram showing an apparatus for acquiring electric activity used in an example.

FIG. 6 shows an apparatus for acquiring electric activity used in the example. This apparatus 112 includes 2-axis bases 114 and 116, and a tip portion of the base 114 that reaches a deeper site provides a recording electrode (first electrode) 120. The recording electrode 120 is formed by using a metal known as Elgiloy as a base material and coating the base material with glass except for a tip portion of the recording electrode 120. A shaft portion of the base 114 (the whole base 114 except for the tip portion thereof) was 260 micrometers in diameter. Furthermore, the recording electrode 120 had an impedance of 0.8 megaohms (measured at 1 kHz). The apparatus 112 includes a glass tube provided along the base 114 and through which a drug is injected to a local site. Furthermore, the other base 116 is formed of Elgiloy and a pointed tip portion of the base 116 is not coated with glass but is exposed to provide a stimulation electrode (second electrode) (−) 130$a$. A shaft portion of the base 116 is 260 micrometers in diameter. A tungsten wire coated with Teflon (registered trademark) is provided along the other base 116 to serve as a stimulation electrode (+) 130$b$. An impedance between the stimulation electrodes 130$a$ and 130$b$ was 0.4 megaohms (1 kHz), and a distance between the stimulation electrodes was 500 micrometers.

The apparatus 112 was inserted into the brain of a monkey with a skull partly removed so that the insertion was oblique and at 45 degrees to the brain and was directed to the external segment of the globus pallidus (GPe) and an internal segment of the globus pallidus (GPi). FIG. 6 is a cross-sectional view of the brain of the monkey taken along a plane parallel to a front surface of a face (coronal section) and shows that both the recording electrode 120 and the stimulation electrodes 130$a$ and 130$b$ all have reached the internal segment of the globus pallidus (GPi).

Figures 7A, 7B, 7C:
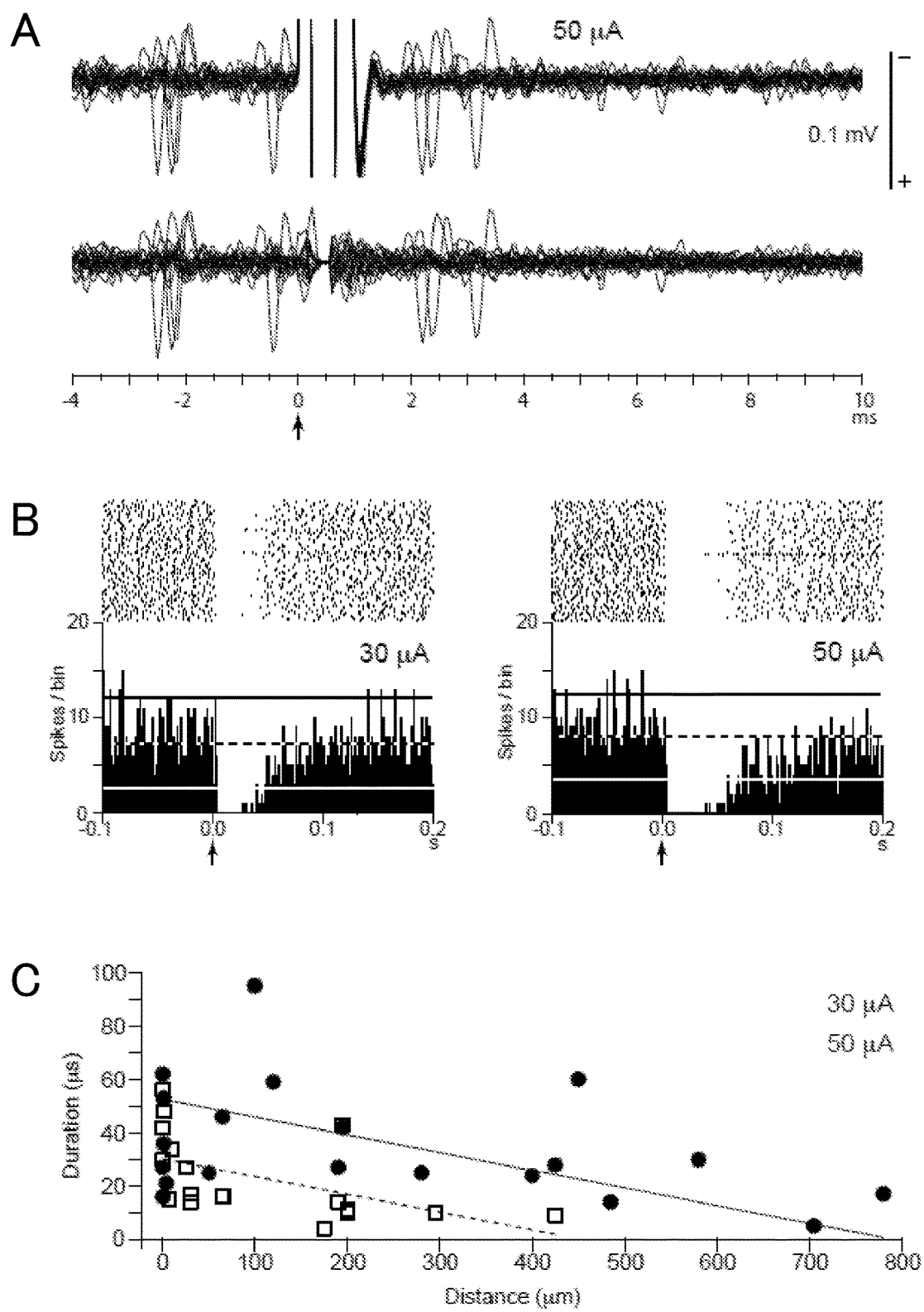
FIG. 7A is a diagram showing the electric activity induced by the application of the single stimulation to the internal segment of the globus pallidus.
FIG. 7B is a diagram showing the electric activity induced by the application of the single stimulation to the internal segment of the globus pallidus.
FIG. 7C is a diagram showing the electric activity induced by the application of the single stimulation to the internal segment of the globus pallidus.

Then, the electric activity of neurons in the internal segment of the globus pallidus (GPi) was recorded when single stimulation (a rectangular wave with a duration of 200 microseconds and a single phase) was applied to the internal segment of the globus pallidus (results of a plurality of stimulations were added together). The results are shown in FIG. 7. FIG. 7A shows raw waveforms that are superimposition of results of a plurality of stimulations (upper section) and the raw waveforms from which noise generated at the time of the stimulations has been removed (lower section). Points in time of the stimulations are shown by arrows. As shown in FIG. 7A, neural activities have been found to be inhibited some time after the stimulation. FIG. 7B shows records of the electric activity shown in FIG. 7A in raster displays (nerve excitation is shown by dots and reactions to the stimulation are aligned at each point in time of stimulation and arranged in order from above to below according to the number of stimulations) and in histograms (created by adding raster displays together). The left figure shows the results of stimulation at a stimulation intensity of 30 microamperes. The right figure shows the results of stimulation at a stimulation intensity of 50 microamperes. As shown in FIG. 7B, the neural activities are inhibited after the stimulation, and a duration of the inhibition increases consistently with stimulation intensity.

Moreover, FIG. 7C shows a figure in which an axis of abscissas indicates a distance between the recording electrode 120 and the stimulation electrode (−) 130a and in which an axis of ordinate indicates the duration of the inhibition. Blank squares indicate the stimulation at 30 microamperes, Filled circles indicate the stimulation at 50 microamperes. As shown in FIG. 7C, the duration of the inhibition increases with decreasing distance (e.g., 0 micrometers, 10 micrometers, 20 micrometers, 50 micrometers, and 70 micrometers) between the recording electrode 120 and the stimulation electrode (−) 130a, However, the inhibition can be observed when the duration of the inhibition is at most 200 micrometers and is appropriately observed when the duration of the inhibition is at most 100 micrometers.

Figures 8A, 8B, 8C:
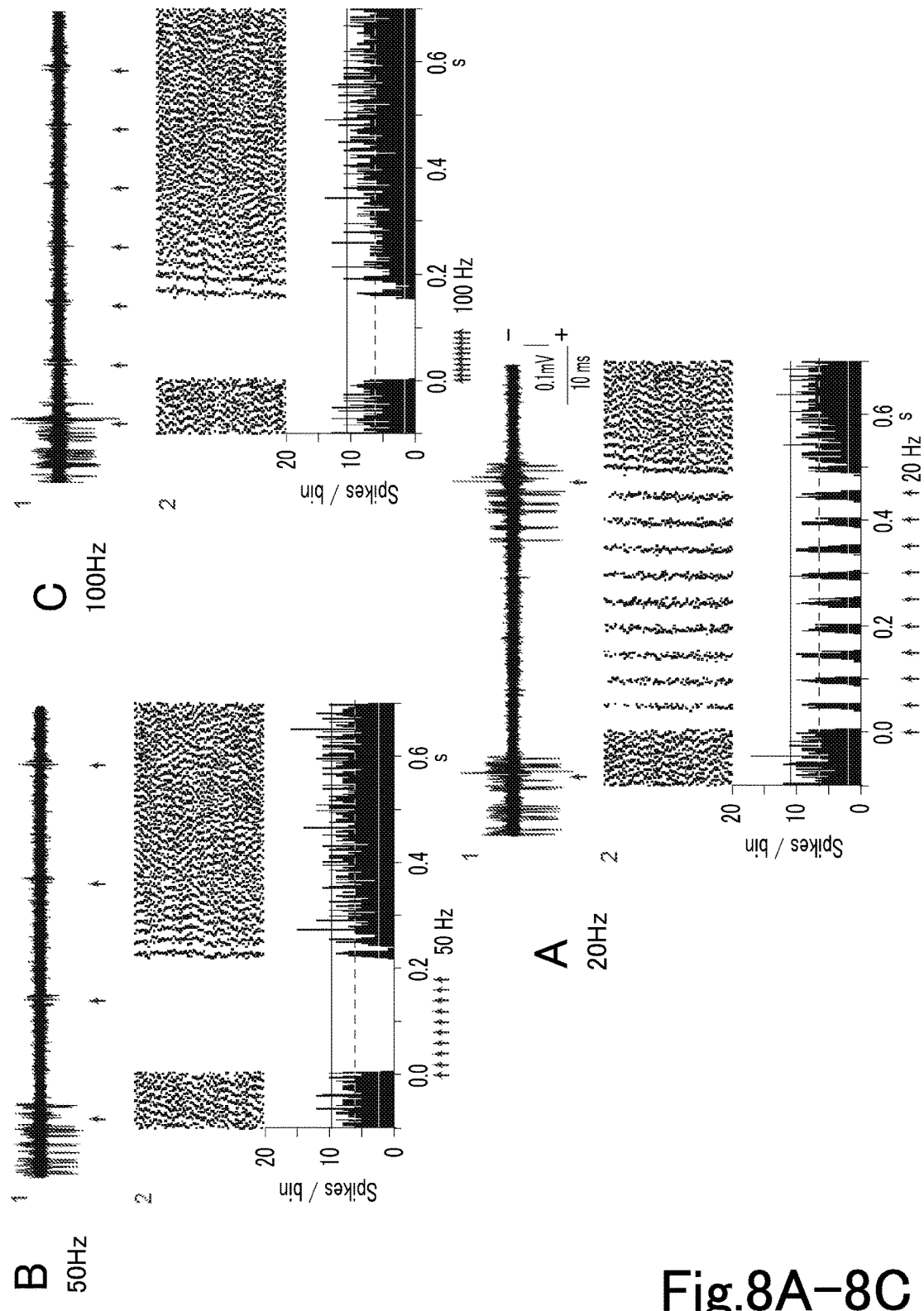
FIG. 8A is a diagram showing the electric activity induced by the application of the repetitive stimulation to the internal segment of the globus pallidus.
FIG. 8B is a diagram showing the electric activity induced by the application of the repetitive stimulation to the internal segment of the globus pallidus.
FIG. 8C is a diagram showing the electric activity induced by the application of the repetitive stimulation to the internal segment of the globus pallidus.

Then, the electric activity of the neurons in the internal segment of the globus pallidus (GPi) in response to repetitive stimulation to the internal segment of the globus pallidus was recorded (results of a plurality of stimulations were added together). The results are shown in FIG. 8. FIGS. 8A to 8C show responses to the repetitive stimulation to the internal segment of the globus pallidus (GPi) was recorded (10 stimulations at 20 Hz, 50 Hz, and 100 Hz; parameters for a stimulation pulse are the same as the parameters for the single stimulation) in raw waveforms, raster displays, and histograms in this order from above to below. A scale for the axis of abscissas differs between the raw waveform and both the raster display and the histogram. Furthermore, the points in time of stimulation are shown by arrows.

As is apparent in FIGS. 8A to 8C, for 10 stimulations at 20 Hz, each stimulation resulted in inhibition, followed by recovery. However, for 10 stimulations at 50 Hz and for 10 stimulations at 100 Hz, inhibitions gradually merged together and the duration of the stimulation was filled with only the inhibition. Furthermore, the inhibition has been found to last some time after end of the stimulation.

Furthermore, the electric activity of neurons in the external segment of the globes pallidus (GPe) in response to single stimulation and repetitive stimulation to the external segment of the globus pallidus was recorded. Results are shown in FIG. 9. FIG. 9A indicates that, in response to the single stimulation, the neurons in the external segment of the globus pallidus exhibit inhibition and then excitation (upper section) and that the excitation is enhanced by 10 stimulations at 50 Hz and 10 stimulations at 100 Hz (middle section and lower section). The neurons in the external segment of the globus pallidus exhibit excitation even after end of the stimulation, and the excitation is considerably intense under the 100-Hz stimulation (lower section in FIG. 9A).

Figure 9B:
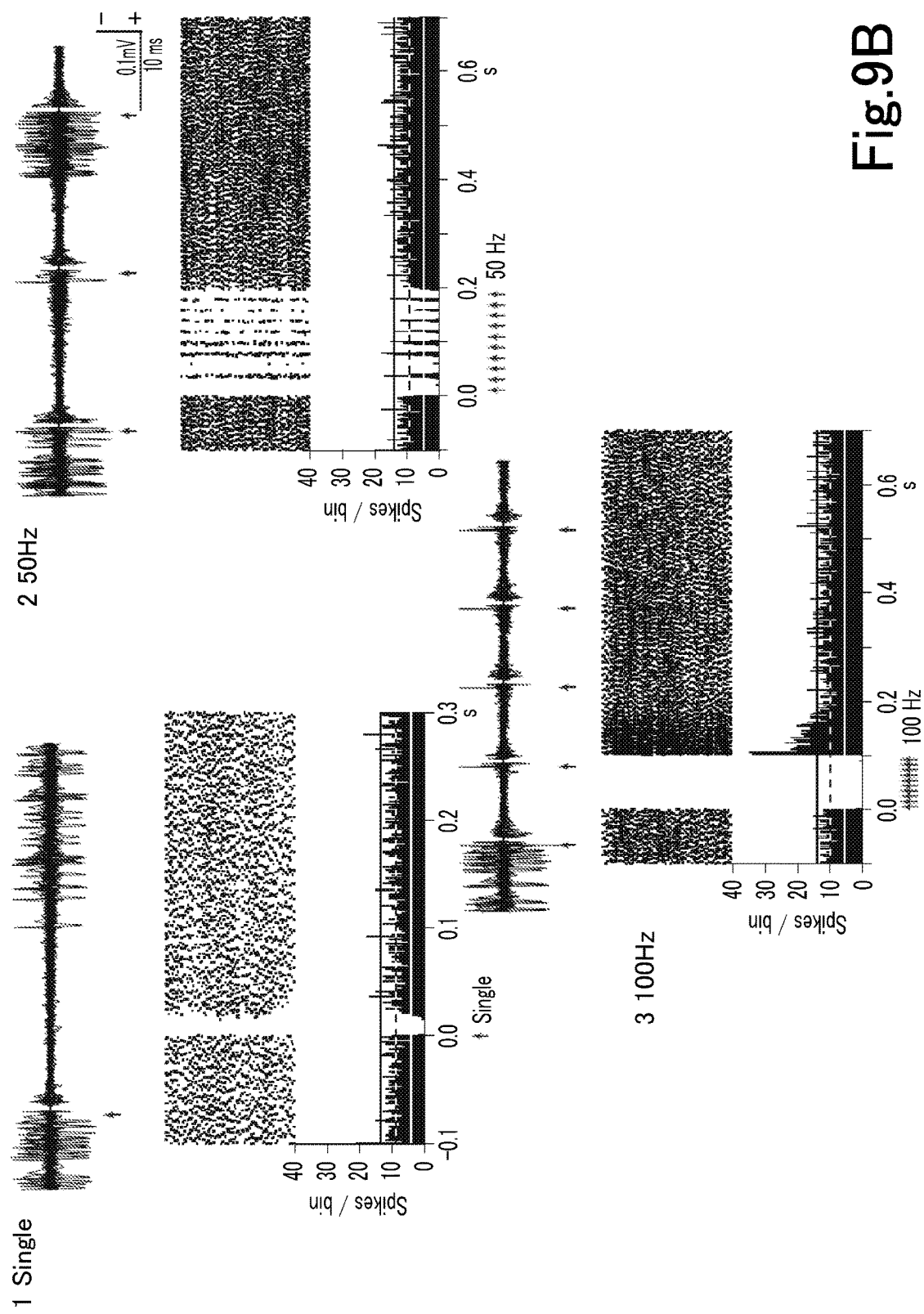
FIG. 9B is a diagram showing the electric activity induced by the application of the single stimulation and the repetitive stimulation to the external segment of the globus pallidus.

Furthermore, FIG. 9B shows records of neurons in the external segment of the globus pallidus (GPe) mainly exhibiting inhibition. Approximately half the neurons in the external segment of the globes pallidus (GPe) exhibit this pattern. For 10 stimulations at 100 Hz, even these neurons exhibited excitation after end of the stimulation.

It has been found from the above-described example that the internal segment and the external segment of the globus pallidus, which are component nuclei of the basal ganglia, exhibit different electric activity patterns when subjected to the electric stimulation. It has also been found that the internal segment and the external segment of the globus pallidus exhibit different patterns according to the stimulation form such as the single stimulation or the repetitive stimulation or the frequency. It has thus been found that nucleus-specific electric activity patterns can be obtained by application of one or more types of electric stimulations. It has also been found that an increase in variation of the electric stimulation enables various electric activity patterns to acquired, allowing electric activity patterns to be more specifically acquired. It has also been found that the use of raster displays and histograms besides raw waveforms enables the electric activity to be characterized and that a combination of raw waveforms, raster displays, and histograms allows a more specific electric activity to be easily and accurately acquired.

What is claimed is:

1. A method of using an electric activity information in brain, the method using an apparatus, which includes:
    one or more needle-like base enabled to be inserted to the brain;
    a first electrode a first impedance and acquiring an input of an electric activity of a brain tissue with which the first electrode comes into contact and being provided at a portion of the at least one of the one or more bases;
    a pair of second electrodes having a second impedance lower than the first impedance, applying an electric stimulation to the brain tissue and being provided at portions of the at least one of the one or more bases,
    wherein the first electrode is positioned at a tip portion of the at least one of the one or more bases and the second electrodes are aligned along the long axis of at least one of the one or more bases at positions closer to a proximal end than the first electrode, and configured to be provided within a range in which the second electrodes are placed in the same nucleus as the first electrode is placed,
    and the method comprising:
    inserting the at least one or more base into the brain so that the first electrode and the second electrodes are positioned within the same nucleus of the brain;
    outputting one or more electric stimulations of one or more single stimulations and/or one or more repetitive stimulations from the second electrodes at the nucleus in which the second electrode is placed;
    receiving one or more electric activities in the brain tissue induced based on the one or more electric stimulations output by the first electrode; and
    comparing one or more inhibition and/or excitation patterns based on the one or more electric activities with one or more nucleus-specific inhibition and/or excitation patters pre-acquired by stimulating and receiving within the specific nucleus and identifying whether the first electrode is positioned at the specific nucleus.

2. The method according to claim 1, wherein the deciding analyzes the one or more electric activities in one or more forms of selected from raw waveforms, raster displays, and histograms based on the action potential.

3. The method according to claim 1, wherein the electric activity information is new information on the nucleus-specific electric activity, a disease-specific electric activity, or an individual-specific electric activity.

4. The method according to claim 1, further comprising: stimulating a target site in the brain based on the determined the first electrode's position.

5. The method according to claim 1, further comprising: improving or treating the electric activity of the brain tissue by stimulating a target site in the brain based on the determined the first electrode's position.

6. The method according to claim 1, the apparatus further comprising:
a tube through which a drug can be injected on the at least one of the one or more bases and the method further comprising injecting the drug to a target site.

7. The method according to claim 1, the apparatus further comprising:
an electrode that enables a tissues to be solidified or cauterized on the at least one of the one or more bases and the method further comprising destroying a target site.

8. The method according to claim 1, wherein the tissue is one selected from the group consisting of an internal segment of a globus pallidus, an external segment of the globus pallidus, a putamen, a caudate nucleus, a ventral striatum, a ventral pallidum, a subthalamic nucleus, and a substantia nigra.

9. The method according to claim 8, wherein the tissue is an internal segment of a globus pallidus and/or an external segment of the globus pallidus.

10. The method according to claim 1, wherein the second electrodes are provided on the base provided with the first electrode at the tip portion.

11. The method according to claim 1, wherein a distance between the first electrode and the second electrode closer to the first electrode along the long axis direction of the base provided with the first electrode is at most 200 micrometers.

12. A system for carrying out the method according to claim 1, the system comprising:
an input-output apparatus which comprises one or more needle-like base enabled to be inserted to the brain;
a first electrode a first impedance and acquiring an input of an electric activity of a brain tissue with which the first electrode comes into contact and being provided at a portion of the at least one of the one or more bases;
a pair of second electrodes having a second impedance lower than the first impedance, applying an electric stimulation to the brain tissue and being provided at portions of the at least one of the one or more bases,
wherein the first electrode is positioned at a tip portion of the at least one of the one or more bases and the second electrodes are aligned along the long axis of at least one of the one or more bases at positions closer to a proximal end than the first electrode; and
a control apparatus that controls the input-output apparatus outputting one or more electric stimulations of one or more single stimulations and/or one or more repetitive stimulations and receiving one or more electric activities in the tissue induced based on the one or more electric stimulations output from the second electrodes; and decides the one or more electric activities in the tissue as brain-site specific electric activity information.

* * * * *